United States Patent
Kanjolia et al.

(10) Patent No.: US 10,221,481 B2
(45) Date of Patent: Mar. 5, 2019

(54) METAL COMPLEXES CONTAINING AMIDOIMINE LIGANDS

(71) Applicant: SAFC HITECH INC., Haverhill, MA (US)

(72) Inventors: Ravi Kanjolia, North Andover, MA (US); Shaun Garratt, Wirral (GB); David Thompson, San Jose, CA (US); Jeffrey Anthis, San Jose, CA (US)

(73) Assignee: MERCK PATENT GMBH, Darmstadt (DE)

( * ) Notice: Subject to any disclaimer, the term of this patent is extended or adjusted under 35 U.S.C. 154(b) by 99 days.

(21) Appl. No.: 15/032,559

(22) PCT Filed: Oct. 24, 2014

(86) PCT No.: PCT/US2014/062108
§ 371 (c)(1),
(2) Date: Apr. 27, 2016

(87) PCT Pub. No.: WO2015/065823
PCT Pub. Date: May 7, 2015

(65) Prior Publication Data
US 2016/0273106 A1 Sep. 22, 2016
US 2018/0291503 A2 Oct. 11, 2018

Related U.S. Application Data

(60) Provisional application No. 61/896,218, filed on Oct. 28, 2013.

(51) Int. Cl.
*C23C 16/00* (2006.01)
*C23C 16/455* (2006.01)
(Continued)

(52) U.S. Cl.
CPC ...... *C23C 16/45553* (2013.01); *C07F 13/005* (2013.01); *C23C 16/18* (2013.01);
(Continued)

(58) Field of Classification Search
CPC .......................... C07C 251/08; C07F 16/005
See application file for complete search history.

(56) References Cited

U.S. PATENT DOCUMENTS

2013/0164456 A1* 6/2013 Winter .................... C23C 16/34
427/535
2013/0251903 A1* 9/2013 Han ........................ C23C 16/18
427/252

FOREIGN PATENT DOCUMENTS

| CN | 102250152 A | 11/2011 |
| CN | 103298971 A | 9/2013 |

(Continued)

OTHER PUBLICATIONS

Muresan et al. Bis(alpha-diimine)iron Complexes: Electronic Structure Determination by Spectroscopy and Broken Symmetry Density Functional Theoretical Calculations, Inorg. Chem. 2008, 47, pp. 4579-4590. (Year: 2008).*

(Continued)

*Primary Examiner* — Kelly M Gambetta
(74) *Attorney, Agent, or Firm* — Harness, Dickey and Pierce, P.L.C.

(57) ABSTRACT

Metal complexes containing one or more amidoimine ligands, methods of making such metal complexes, and methods of using such metal complexes to prepare metal-containing films are provided.

(Continued)

US 10,221,481 B2
Page 2

(51) Int. Cl.
 C23C 16/40 (2006.01)
 H01L 21/285 (2006.01)
(52) U.S. Cl.
 CPC .............. *C23C 16/34* (2013.01); *C23C 16/40* (2013.01); *H01L 21/28556* (2013.01); *H01L 21/28568* (2013.01)

(56) References Cited

FOREIGN PATENT DOCUMENTS

| EP | 2636674 A1 | 9/2013 | | |
|---|---|---|---|---|
| WO | WO-9830609 A1 | 7/1998 | | |
| WO | WO-2012/060428 A1 | 5/2012 | | |
| WO | WO-2012/067439 A2 | 5/2012 | | |
| WO | WO-2012067439 A2 * | 5/2012 | ............. | C23C 16/18 |
| WO | WO-2012/176988 A1 | 12/2012 | | |

OTHER PUBLICATIONS

Search Report dated Sep. 26, 2017 issued in TW Patent Application No. 103137274.
Rosenberger, et al.: "Diazadien-Komplexe des Rutheniums. XIII. Bis(diazadien)ruthenium: Isomerisierung, Hydrierung, Metallierung; Struktur eines Kalium(tmeda)2-ruthenats(0)", Journal of Organometallic Chemistry, Elsevier_Sequoia S.A., Lausanne, CH, vol. 411, No. 3, Jan. 1, 1991 (Jan. 1, 1991), pp. 445-456, XP002410474, ISSN: 0022-328X, DOI: 10.1016/0022-328X(91)83049-A.
Anna Eissler, et al.:"[alpha]-Dialdimine Complexes of Rhodium(I) and Iridium(I): Their Reactivity with Dioxygen and Dihydrogen", European Journal of Inorganic Chemistry, vol. 2013, No. 27, Sep. 10, 2013 (Sep. 10, 2013), pp. 4775-4788, XP055160421, ISSN: 1434-1948, DOI: 10.1002/ejic.201300625.
Peter B.. Kraikivskii, et al.: "Formation of the paramagletic Ni(I)-allyl complex in the Ni(allyl)(2,6-diisopropylphenyl)diazabutadiene system", Journal of Organometallic Chemistry, Elsevier-Sequoia S.A., Lausanne, CH, vol. 696, No. 22, Jul. 18, 2011 (Jul. 18, 2011), pp. 3483-3490, XP028295566, ISSN: 0022-328X, DOI: 10.1016/J.JORGANCHEM.2011.07.023 [retrieved on Jul. 23, 2011].
Lee, J., et al. (2008), "Unsymmetrical bidentate ligands of α-aminoaldimines leading to sterically controlled selectivity of geometrical isomerism in square planar coordination", *Dalton Trans.,* 5945-5956.
Search Report dated Oct. 20, 2016 issued in SG Patent Application No. 11201603379X.
Written Opinion dated Dec. 14, 2016 issued in SG Patent Application No. 11201603379X.
Yang, F., et al. (2009), "Kinetic and Mechanistic Studies of Geometrical Isomerism in Neutral Square-Planar Methylpalladium Complexes Bearing Unsymmetrical Bidentate Ligands of α-Aminoaldimines", *Inorganic Chemistry,* 48: 7639-7644.
Yang, F., et al. (2009), "Nickel catalysts bearing bidentate α-aminoaldimines for ethylene polymerization—independent and cooperative structure/reactivity relationship resulting from unsymmetric square planar coordination", *Dalton Trans.,* 1243-1250.
Borisov, V.O., et al., (1995), Kinetics of Nickel Deposition from Ni(HL*)₂ Vapor.

* cited by examiner

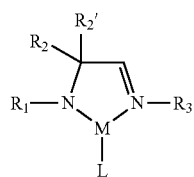

(I)

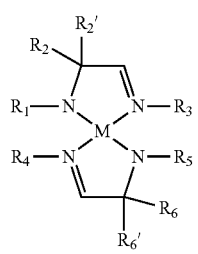

(IA)

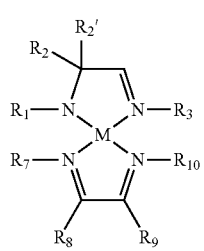

(IB)

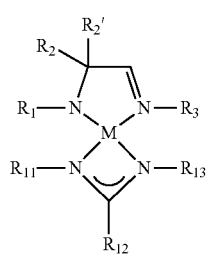

(IC)

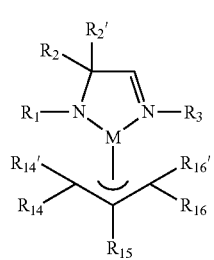

(ID)

25 Claims, 2 Drawing Sheets

(51) Int. Cl.
 C07F 13/00 (2006.01)
 C23C 16/18 (2006.01)
 C23C 16/34 (2006.01)

METAL COMPLEXES CONTAINING AMIDOIMINE LIGANDS

CROSS-REFERENCE TO RELATED APPLICATIONS

This patent application is a U.S. national stage filing under 35 U.S.C. § 371 of International Application No. PCT/US2014/062108 filed on of 24 Oct. 2014, which claims the benefit of U.S. Provisional Patent Application No. 61/896,218 filed on 28 Oct. 2013. The entire disclosures of each of the above recited applications are incorporated herein by reference.

TECHNICAL FIELD

The present technology relates generally to metal complexes including at least one amidoimine ligand, methods of making such metal complexes, and methods of preparing metal-containing thin films using such metal complexes.

BACKGROUND

Various precursors are used to form thin films and a variety of deposition techniques have been employed. Such techniques include reactive sputtering, ion-assisted deposition, sol-gel deposition, CVD (also known as metalorganic CVD or MOCVD), and ALD (also known as atomic layer epitaxy). CVD and ALD processes are being increasingly used as they have the advantages of good compositional control, high film uniformity, good control of doping and, significantly, they provide excellent conformal step coverage on highly non-planar geometries associated with modern microelectronic devices.

CVD is a chemical process whereby precursors are used to form a thin film on a substrate surface. In a typical CVD process, the precursors are passed over the surface of a substrate (e.g., a wafer) in a low pressure or ambient pressure reaction chamber. The precursors react and/or decompose on the substrate surface creating a thin film of deposited material. Volatile by-products are removed by gas flow through the reaction chamber. The deposited film thickness can be difficult to control because it depends on coordination of many parameters such as temperature, pressure, gas flow volumes and uniformity, chemical depletion effects, and time.

ALD is also a method for the deposition of thin films. It is a self-limiting, sequential, unique film growth technique based on surface reactions that can provide precise thickness control and deposit conformal thin films of materials provided by precursors onto surfaces substrates of varying compositions. In ALD, the precursors are separated during the reaction. The first precursor is passed over the substrate surface producing a monolayer on the substrate surface. Any excess unreacted precursor is pumped out of the reaction chamber. A second precursor is then passed over the substrate surface and reacts with the first precursor, forming a second monolayer of film over the first-formed monolayer of film on the substrate surface. This cycle is repeated to create a film of desired thickness.

Thin films, and in particular thin metal-containing films, have a variety of important applications, such as in nanotechnology and the fabrication of semiconductor devices. Examples of such applications include high-refractive index optical coatings, corrosion-protection coatings, photocatalytic self-cleaning glass coatings, biocompatible coatings, dielectric capacitor layers and gate dielectric insulating films in field-effect transistors (FETs), capacitor electrodes, gate electrodes, adhesive diffusion barriers, and integrated circuits. Dielectric thin films are also used in microelectronics applications, such as the high-κ dielectric oxide for dynamic random access memory (DRAM) applications and the ferroelectric perovskites used in infrared detectors and non-volatile ferroelectric random access memories (NV-Fe-RAMs). The continual decrease in the size of microelectronic components has increased the need for improved thin film technologies.

Technologies relating to the preparation of manganese-containing thin films are of particular interest. For example, manganese-containing films have found numerous practical applications in areas such as catalysts, batteries, memory devices, displays, sensors, and nano- and microelectronics. In the case of electronic applications, elemental manganese metal or manganese nitride films can act as barriers layers such that they prevent diffusion of copper interconnects into the underlying silicon dioxide substrate (e.g., self-forming diffusion barrier layers). While barrier layers based on other metal systems may be employed to inhibit copper atom diffusion, there remain significant challenges with such systems. For example, tantalum nitride provides a suitable copper diffusion barrier at film thicknesses greater than about 10 Å—a thickness where such films are continuous—thinner films of tantalum nitride are not continuous, and as such, do not provide adequate diffusion barrier properties. This is a significant hurdle for smaller node devices (less than ~32 nm) where thinner diffusion barriers are required. Evidence suggests that manganese nitride diffusion barriers may be an attractive alternative to tantalum-based diffusion barriers in the back-end-of-line copper interconnections in next generation devices. However, there are few examples of manganese precursors which can provide high quality and/or high purity films of elemental manganese or manganese nitride. Potential manganese precursor candidates often suffer from poor vapor pressures and reaction rates, and/or provide manganese-containing films with undesirable morphology. Accordingly, there exists significant interest in the development of manganese complexes with performance characteristics which make them suitable for use as precursor materials in vapor deposition processes to prepare manganese nitride and other manganese-containing films. For example, manganese precursors with improved performance characteristics (e.g., thermal stabilities, vapor pressures, deposition rates, and barrier properties of films produced therefrom) are needed, as are methods of depositing thin films from such precursors.

SUMMARY

According to one aspect, a metal complex of Formula I is provided:

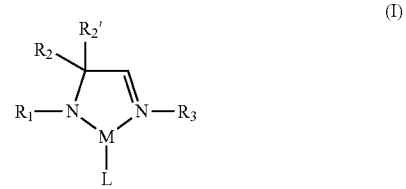

wherein $R_1$, $R_2$, $R_{2'}$, and $R_3$ are independently selected from the group consisting of hydrogen, alkyl, and aryl; M is a metal selected from Groups 7-10 of the periodic table or is copper; and L comprises at least one ligand.

In some embodiments of the metal complex of Formula I, M is selected from the group consisting of manganese, cobalt, nickel, and copper. In particular embodiments, M is manganese.

In some embodiments of the metal complex of Formula I, $R_1$, $R_2$, $R_{2'}$, and $R_3$ are independently selected from the group consisting of hydrogen, $C_1$-$C_4$-alkyl, and $C_6$-$C_{10}$-aryl. In particular embodiments, $R_1$, $R_2$, $R_{2'}$, and $R_3$ are independently selected from the group consisting of hydrogen, methyl, ethyl, propyl, isopropyl, butyl, sec-butyl, tert-butyl, and phenyl. In other embodiments, $R_2$ and $R_{2'}$ are each methyl.

In some embodiments of the metal complex of Formula I, L comprises at least one monodentate or bidentate ligand. In such embodiments, L may be, for example, an amidoimine ligand, a diazabutadiene (DAD) ligand, an amidinate (AMD) ligand or an allyl ligand. In one or more embodiments, L is an $\eta^3$-allyl ligand.

According to another aspect, a metal complex of Formula IA is provided:

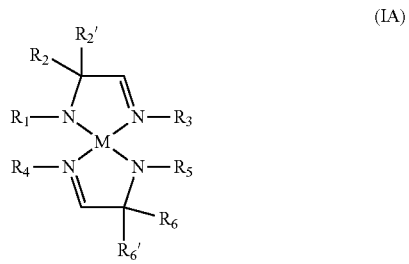

(IA)

wherein $R_1$, $R_2$, $R_{2'}$, $R_3$, $R_4$, $R_5$, $R_6$, and $R_{6'}$ are independently selected from the group consisting of hydrogen, alkyl, and aryl; and M is a metal selected from Groups 7-10 of the periodic table or is copper.

In some embodiments of the metal complex of Formula IA, M is selected from the group consisting of manganese, cobalt, nickel, and copper. In particular embodiments, M is manganese.

In some embodiments of the metal complex of Formula IA, $R_1$, $R_2$, $R_{2'}$, $R_3$, $R_4$, $R_5$, $R_6$, and $R_{6'}$ are independently selected from the group consisting of hydrogen, $C_1$-$C_4$-alkyl, and $C_6$-$C_{10}$-aryl. In particular embodiments, $R_1$, $R_2$, $R_{2'}$, $R_3$, $R_4$, $R_5$, $R_6$ and $R_{6'}$ are independently selected from the group consisting of hydrogen, methyl, ethyl, propyl, isopropyl, butyl, sec-butyl, tert-butyl, and phenyl.

In some embodiments of the metal complex of Formula IA, $R_2$, $R_{2'}$, $R_6$, and $R_{6'}$ are each methyl.

In some embodiments, the metal complex of Formula IA is a homoleptic complex, such that $R_1=R_5$, $R_2=R_6$, $R_{2'}=R_{6'}$, and $R_3=R_4$.

According to another aspect, a metal complex of Formula IB is provided:

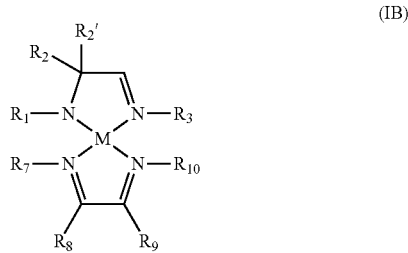

(IB)

wherein $R_1$, $R_2$, $R_{2'}$, $R_3$, $R_7$, $R_8$, $R_9$, and $R_{10}$ are independently selected from the group consisting of hydrogen, alkyl, and aryl; and M is a metal selected from Groups 7-10 of the periodic table or is copper.

In some embodiments of the metal complex of Formula IB, M is selected from the group consisting of manganese, cobalt, nickel, and copper. In particular embodiments, M is manganese.

In some embodiments of the metal complex of Formula IB, $R_1$, $R_2$, $R_{2'}$, $R_3$, $R_7$, $R_8$, $R_9$, and $R_{10}$ are independently selected from the group consisting of hydrogen, $C_1$-$C_4$-alkyl, and $C_6$-$C_{10}$-aryl. In particular embodiments, $R_1$, $R_2$, $R_{2'}$, $R_3$, $R_7$, $R_8$, $R_9$, and $R_{10}$ are independently selected from the group consisting of hydrogen, methyl, ethyl, propyl, isopropyl, butyl, sec-butyl, tert-butyl, and phenyl.

In some embodiments of the metal complex of Formula IB, $R_2$ and $R_{2'}$ are each methyl.

In some embodiments of the metal complex of Formula IB, $R_8$ and $R_9$ are each hydrogen.

According to another aspect, a metal complex of Formula IC is provided:

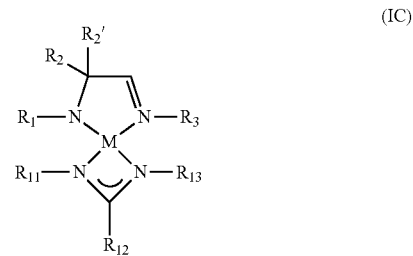

(IC)

wherein $R_1$, $R_2$, $R_{2'}$, $R_3$, $R_{11}$, $R_{12}$, and $R_{13}$ are independently selected from the group consisting of hydrogen, alkyl, and aryl; and M is a metal selected from Groups 7-10 of the periodic table or is copper.

In some embodiments of the metal complex of Formula IC, M is selected from the group consisting of manganese, cobalt, nickel, and copper. In particular embodiments, M is manganese.

In some embodiments of the metal complex of Formula IC, $R_1$, $R_2$, $R_{2'}$, $R_3$, $R_{11}$, $R_{12}$, and $R_{13}$ are independently selected from the group consisting of hydrogen, $C_1$-$C_4$-alkyl, and $C_6$-$C_{10}$-aryl. In particular embodiments, $R_1$, $R_2$, $R_{2'}$, $R_3$, $R_{11}$, $R_{12}$, and $R_{13}$ are independently selected from the group consisting of hydrogen, methyl, ethyl, propyl, isopropyl, butyl, sec-butyl, tert-butyl, and phenyl.

In some embodiments of the metal complex of Formula IC, $R_2$ and $R_{2'}$ are each methyl.

According to another aspect, a metal complex of Formula ID is provided:

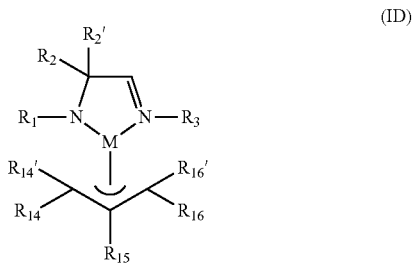

(ID)

wherein $R_1$, $R_2$, $R_{2'}$, and $R_3$ are independently selected from the group consisting of hydrogen, alkyl, and aryl; $R_{14}$, $R_{14'}$, $R_{15}$, $R_{16}$, and $R_{16'}$ are independently selected from the group consisting of hydrogen, alkyl, aryl, and silyl; and M is a metal selected from Groups 7-10 of the periodic table or is copper.

In some embodiments of the metal complex of Formula ID, M is selected from the group consisting of manganese, cobalt, nickel, and copper. In particular embodiments, M is manganese.

In some embodiments of the metal complex of Formula ID, $R_1$, $R_2$, $R_{2'}$, and $R_3$ are independently selected from the group consisting of hydrogen, $C_1$-$C_4$-alkyl, $C_6$-$C_{10}$-aryl; and $R_{14}$, $R_{14'}$, $R_{15}$, $R_{16}$, and $R_{16'}$ are independently selected from the group consisting of hydrogen, $C_1$-$C_4$-alkyl, $C_6$-$C_{10}$-aryl, and tri($C_1$-$C_4$-alkyl)silyl. In particular embodiments, $R_1$, $R_2$, $R_{2'}$, and $R_3$ are independently selected from the group consisting of hydrogen, methyl, ethyl, propyl, isopropyl, butyl, sec-butyl, tert-butyl, and phenyl; and $R_{14}$, $R_{14'}$, $R_{15}$, $R_{16}$, and $R_{16'}$ are independently selected from the group consisting of hydrogen, methyl, ethyl, propyl, isopropyl, butyl, sec-butyl, tert-butyl, phenyl, and trimethylsilyl.

In some embodiments of the metal complex of Formula ID, $R_2$ and $R_{2'}$ are each methyl.

In another aspect, a solvate of any one of the metal complexes of Formulas I, IA, IB, IC, or ID is provided. In some embodiments, the solvate includes a solvent coordinated (ligated) to the metal center of the metal complex. In some embodiments, the solvate is an ether solvate, an amine solvate or a hydrocarbon solvate.

Other aspects of the present technology pertain to methods of making the metal complexes described herein—including those of Formulas I, IA, IB, IC, or ID, methods of making intermediates to such metal complexes, and vapor phase deposition methods employing such metal complexes as precursor materials as to provide metal-containing films.

DETAILED DESCRIPTION

Figure 1:
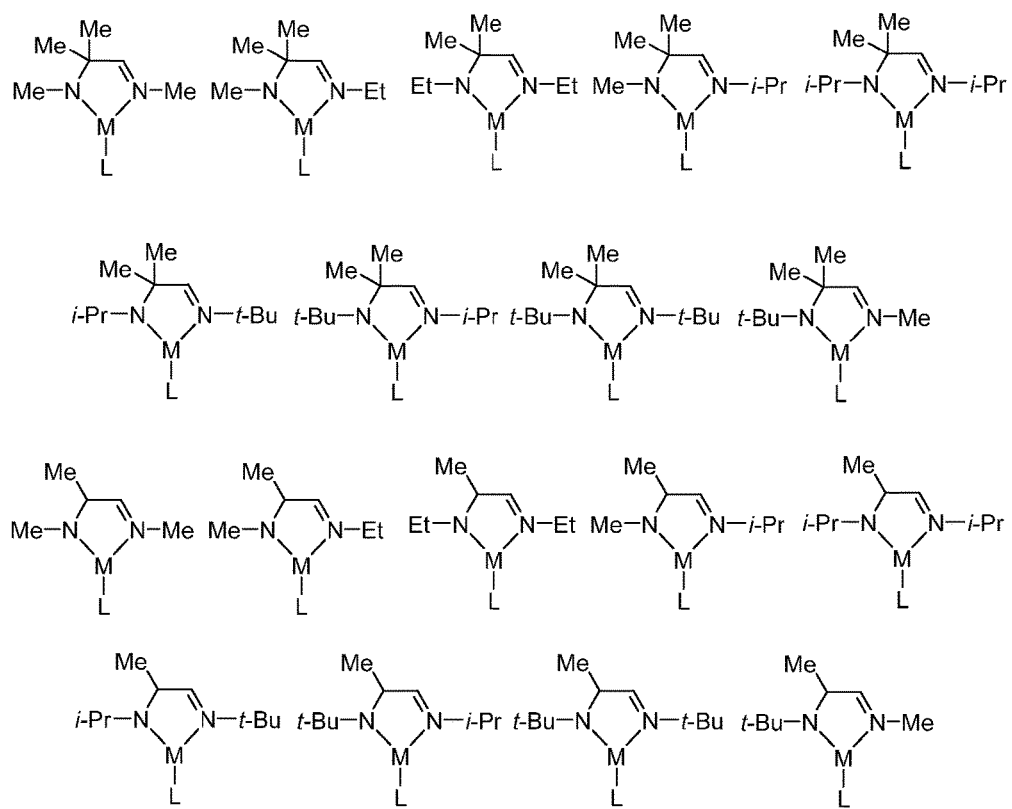
FIG. 1 illustrates various embodiments of metal complexes of Formula I, where M is a metal selected from Groups 7-10 of the periodic table or is copper.

Before describing several exemplary embodiments of the present technology, it is to be understood that the technology is not limited to the details of construction or process steps set forth in the following description. The present technology is capable of other embodiments and of being practiced or being carried out in various ways. It is also to be understood that the metal complexes and other chemical compounds may be illustrated herein using structural formulas which have a particular stereochemistry. These illustrations are intended as examples only and are not to be construed as limiting the disclosed structure to any particular stereochemistry. Rather, the illustrated structures are intended to encompass all such metal complexes and chemical compounds having the indicated chemical formula.

In various aspects, metal complexes, methods of making such metal complexes, and methods of using such metal complexes to form thin metal-containing films via vapor deposition processes, are provided.

As used herein, the terms "metal complex" (or more simply, "complex") and "precursor" are used interchangeably and refer to metal-containing molecule or compound which can be used to prepare a metal-containing film by a vapor deposition process such as, for example, ALD or CVD. The metal complex may be deposited on, adsorbed to, decomposed on, delivered to, and/or passed over a substrate or surface thereof, as to form a metal-containing film. In one or more embodiments, the metal complexes disclosed herein are manganese complexes.

As used herein, the term "metal-containing film" includes not only an elemental metal film as more fully defined below, but also a film which includes a metal along with one or more elements, for example a metal oxide film, metal nitride film, metal silicide film, and the like. As used herein, the terms "elemental metal film" and "pure metal film" are used interchangeably and refer to a film which consists of, or consists essentially of, pure metal. For example, the elemental metal film may include 100% pure metal or the elemental metal film may include at least about 90%, at least about 95%, at least about 96%, at least about 97%, at least about 98%, at least about 99%, at least about 99.9%, or at least about 99.99% pure metal along with one or more impurities. Unless context dictates otherwise, the term "metal film" shall be interpreted to mean an elemental metal film. In some embodiments, the metal-containing film is an elemental manganese film. In other embodiments, the metal-containing film is manganese oxide, manganese nitride, or manganese silicide film. Such manganese-containing films may be prepared from various manganese complexes described herein.

As used herein, the term "vapor deposition process" is used to refer to any type of vapor deposition technique, including but not limited to, CVD and ALD. In various embodiments, CVD may take the form of conventional (i.e., continuous flow) CVD, liquid injection CVD, or photo-assisted CVD. CVD may also take the form of a pulsed technique, i.e., pulsed CVD. In other embodiments, ALD may take the form of conventional (i.e., pulsed injection) ALD, liquid injection ALD, photo-assisted ALD, plasma-assisted ALD, or plasma-enhanced ALD. The term "vapor deposition process" further includes various vapor deposition techniques described in *Chemical Vapour Deposition: Precursors, Processes, and Applications*; Jones, A. C.; Hitchman, M. L., Eds. The Royal Society of Chemistry: Cambridge, 2009; Chapter 1, pp 1-36.

The term "alkyl" (alone or in combination with another term(s)) refers to a saturated hydrocarbon chain of 1 to about 12 carbon atoms in length, such as, but not limited to, methyl, ethyl, propyl, butyl, pentyl, hexyl, heptyl, octyl, decyl, and so forth. The alkyl group may be straight-chain or branched-chain. "Alkyl" is intended to embrace all structural isomeric forms of an alkyl group. For example, as used herein, propyl encompasses both n-propyl and isopropyl; butyl encompasses n-butyl, sec-butyl, isobutyl and tert-butyl. Further, as used herein, "Me" refers to methyl, "Et" refers to ethyl, "i-Pr" refers to isopropyl, "t-Bu" refers to tert-butyl, and "Np" refers to neopentyl. In some embodiments, alkyl groups are $C_1$-$C_8$- or $C_1$-$C_4$-alkyl groups.

The term "solvate," in relation to any metal complex described herein, refers to a metal complex that further includes a stoichiometric or non-stoichiometric amount of solvent associated with the metal complex. For instance, the solvent may be covalently bound to the metal center of the metal complex (e.g., as a ligand) or otherwise associated with the metal complex, such as for example, through non-covalent intermolecular forces (e.g., as a solvent of crystallization).

All of the metal complexes disclosed herein comprise at least one amidoimine ligand. Where a given metal complex comprises more than one amidoimine ligand, for instance two amidoimine ligands, the amidoimine ligand may be the same or different at each occurrence. The amidoimine ligand features a formally anionic amine group (i.e., an amido group) and a formally neutral imine group, as represented by the compound of Formula II:

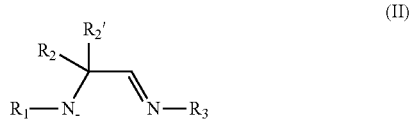

(II)

wherein $R_1$, $R_2$, $R_{2'}$, and $R_3$ are independently selected from the group consisting of hydrogen, alkyl, and aryl. The amidoimine ligand coordinates to the metal center of the metal complex through the nitrogen atoms of the amido and imine groups. As further described herein, the metal complexes may include other ligands bound to the metal center, in addition to the one or more amidoimine ligands. While not wishing to be bound by any particular theory, it is believed that such amidoimine ligands will offer benefits of amido and beta-diimines, such as all nitrogen bonding and metal center stabilization. At the same time, the amidoimine ligands are thought to be more labile, due to the relatively weak imine-metal bond. In this regard, metal complexes of such amidoimine ligands are excellent candidates for preparation of thin metal-containing films in various vapor deposition processes.

Therefore, according to one aspect, a metal complex of Formula I is provided:

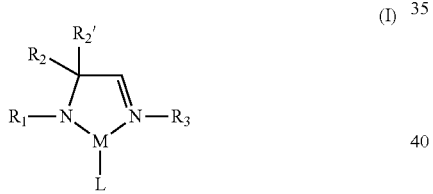

(I)

wherein $R_1$, $R_2$, $R_{2'}$, and $R_3$ are independently selected from the group consisting of hydrogen, alkyl, and aryl; M is a metal selected from Groups 7-10 of the periodic table or is copper; and L comprises at least one ligand.

In some embodiments of the metal complex of Formula I, M is selected from the group consisting of manganese, cobalt, nickel, and copper. In particular embodiments, M is manganese.

In some embodiments of the metal complex of Formula I, $R_1$, $R_2$, $R_{2'}$, and $R_3$ are independently selected from the group consisting of hydrogen, $C_1$-$C_4$-alkyl, and $C_6$-$C_{10}$-aryl. In particular embodiments, $R_1$, $R_2$, $R_{2'}$, and $R_3$ are independently selected from the group consisting of hydrogen, methyl, ethyl, propyl, isopropyl, butyl, sec-butyl, tert-butyl, and phenyl. In other embodiments, $R_2$ and $R_{2'}$ are each methyl.

In some embodiments, two, three or four of $R_1$, $R_2$, $R_{2'}$, and $R_3$ are independently alkyl, such as, for example, $C_1$-$C_4$-alkyl. In a particular embodiment, two, three, or four of $R_1$, $R_2$, $R_{2'}$, and $R_3$ are methyl.

In some embodiments, at least one of $R_1$ and $R_3$ are branched alkyl, for example isopropyl or tert-butyl. In other embodiments, $R_1$ and $R_3$ are each independently branched alkyl.

In the metal complex of Formula I, L comprises at least one ligand, which may be monodentate, bidentate, or polydentate. Thus, L may represent one, two, three, or more ligands, each of which may be the same or different at each occurrence, in addition to the amidoimine ligand explicitly shown in the metal complex of Formula I. The number of ligands present in a given metal complex, in addition to the amidoimine ligand, can and will vary depending on various factors, including for example, the identity of the particular ligands and the identity of the particular metal center. In some embodiments, L may be, for example, an amidoimine ligand (e.g., a second amidoimine ligand), a diazabutadiene (DAD) ligand, an amidinate (AMD) ligand, an allyl ligand, or a substituted derivative of any of the foregoing. In particular embodiments, L is an $\eta^3$-allyl ligand. In other embodiments, L is a ligand bound through one or more nitrogen atoms. In yet other embodiments, the metal center of the metal complex of Formula I is bound only to nitrogen atoms only.

According to another aspect, a metal complex comprising two amidoimine ligands is provided which may be represented by the metal complex of Formula IA:

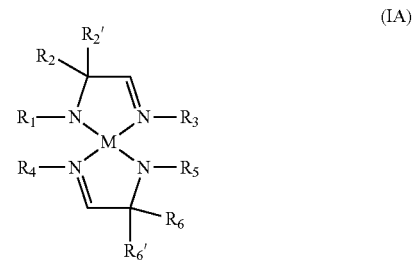

(IA)

wherein $R_1$, $R_2$, $R_{2'}$, $R_3$, $R_4$, $R_5$, $R_6$, and $R_{6'}$ are independently selected from the group consisting of hydrogen, alkyl, and aryl; and M is a metal selected from Groups 7-10 of the periodic table or is copper.

In some embodiments of the metal complex of Formula IA, M is selected from the group consisting of manganese, cobalt, nickel, and copper. In particular embodiments, M is manganese.

In some embodiments of the metal complex of Formula IA, $R_1$, $R_2$, $R_{2'}$, $R_3$, $R_4$, $R_5$, $R_6$, and $R_{6'}$ are independently selected from the group consisting of hydrogen, $C_1$-$C_4$-alkyl, and $C_6$-$C_{10}$-aryl. In particular embodiments, $R_1$, $R_2$, $R_{2'}$, $R_3$, $R_4$, $R_5$, $R_6$, and $R_{6'}$ are independently selected from the group consisting of hydrogen, methyl, ethyl, propyl, isopropyl, butyl, sec-butyl, tert-butyl, and phenyl.

In some embodiments of the metal complex of Formula IA, $R_2$, $R_{2'}$, $R_6$, and $R_{6'}$ are each methyl.

In some embodiments, the metal complex of Formula IA is a homoleptic metal complex, such that $R_1$=$R_5$, $R_2$=$R_6$, $R_{2'}$=$R_{6'}$, and $R_3$=$R_4$. Stated another way, each amidoimine ligand of the metal complex is the same.

According to another aspect, a metal complex comprising an amidoimine ligand and a diazabutadiene ligand is provided which may be represented by the metal complex of Formula IB:

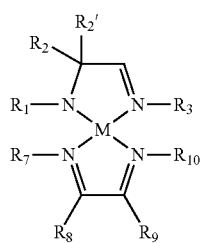

(IB)

wherein $R_1$, $R_2$, $R_{2'}$, $R_3$, $R_7$, $R_8$, $R_9$, and $R_{10}$ are independently selected from the group consisting of hydrogen, alkyl, and aryl; and M is a metal selected from Groups 7-10 of the periodic table or is copper.

In some embodiments of the metal complex of Formula IB, M is selected from the group consisting of manganese, cobalt, nickel, and copper. In particular embodiments, M is manganese.

In some embodiments of the metal complex of Formula IB, $R_1$, $R_2$, $R_{2'}$, $R_3$, $R_7$, $R_8$, $R_9$, and $R_{10}$ are independently selected from the group consisting of hydrogen, $C_1$-$C_4$-alkyl, and $C_6$-$C_{10}$-aryl. In particular embodiments, $R_1$, $R_2$, $R_{2'}$, $R_3$, $R_7$, $R_8$, $R_9$, and $R_{10}$ are independently selected from the group consisting of hydrogen, methyl, ethyl, propyl, isopropyl, butyl, sec-butyl, tert-butyl, and phenyl.

In some embodiments of the metal complex of Formula IB, $R_2$ and $R_{2'}$ are each methyl.

In some embodiments of the metal complex of Formula IB, $R_8$ and $R_9$ are each hydrogen.

In some embodiments of the metal complex of Formula IB, $R_7$ and $R_{10}$ are each alkyl, for example, $C_1$-$C_4$-alkyl.

According to another aspect, a metal complex comprising an amidoimine ligand and an amidinate ligand is provided which may be represented by the metal complex of Formula IC:

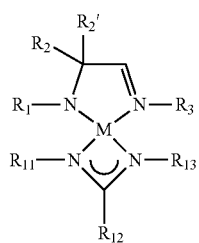

(IC)

wherein $R_1$, $R_2$, $R_{2'}$, $R_3$, $R_{11}$, $R_{12}$, and $R_{13}$ are independently selected from the group consisting of hydrogen, alkyl, and aryl; and M is a metal selected from Groups 7-10 of the periodic table or is copper.

In some embodiments of the metal complex of Formula IC, M is selected from the group consisting of manganese, cobalt, nickel, and copper. In particular embodiments, M is manganese.

In some embodiments of the metal complex of Formula IC, $R_1$, $R_2$, $R_{2'}$, $R_3$, $R_{11}$, $R_{12}$, and $R_{13}$ are independently selected from the group consisting of hydrogen, $C_1$-$C_4$-alkyl, and $C_6$-$C_{10}$-aryl. In particular embodiments, $R_1$, $R_2$, $R_{2'}$, $R_3$, $R_{11}$, $R_{12}$, and $R_{13}$ are independently selected from the group consisting of hydrogen, methyl, ethyl, propyl, isopropyl, butyl, sec-butyl, tert-butyl, and phenyl.

In some embodiments of the metal complex of Formula IC, $R_2$ and $R_{2'}$ are each methyl.

According to another aspect, a metal complex comprising an amidoimine ligand and an $\eta^3$-allyl ligand is provided which may be represented by the metal complex of Formula ID:

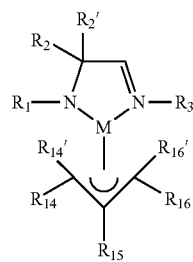

(ID)

wherein $R_1$, $R_2$, $R_{2'}$, and $R_3$ are independently selected from the group consisting of hydrogen, alkyl, and aryl; $R_{14}$, $R_{14'}$, $R_{15}$, $R_{16}$, and $R_{16'}$ are independently selected from the group consisting of hydrogen, alkyl, aryl, and silyl; and M is a metal selected from Groups 7-10 of the periodic table or is copper.

In some embodiments of the metal complex of Formula ID, M is selected from the group consisting of manganese, cobalt, nickel, and copper. In particular embodiments, M is manganese.

In some embodiments of the metal complex of Formula ID, $R_1$, $R_2$, $R_{2'}$, and $R_3$ are independently selected from the group consisting of hydrogen, $C_1$-$C_4$-alkyl, $C_6$-$C_{10}$-aryl; and $R_{14}$, $R_{14'}$, $R_{15}$, $R_{16}$, and $R_{16'}$ are independently selected from the group consisting of hydrogen, $C_1$-$C_4$-alkyl, $C_6$-$C_{10}$-aryl, and tri($C_1$-$C_4$-alkyl)silyl. In particular embodiments, $R_1$, $R_2$, $R_{2'}$, and $R_3$ are independently selected from the group consisting of hydrogen, methyl, ethyl, propyl, isopropyl, butyl, sec-butyl, tert-butyl, and phenyl; and $R_{14}$, $R_{14'}$, $R_{15}$, $R_{16}$, and $R_{16'}$ are independently selected from the group consisting of hydrogen, methyl, ethyl, propyl, isopropyl, butyl, sec-butyl, tert-butyl, phenyl, and trimethylsilyl.

In some embodiments of the metal complex of Formula ID, $R_2$ and $R_{2'}$ are each methyl.

In some embodiments of the metal complex of Formula ID, $R_{14}$, $R_{14'}$, $R_{15}$, $R_{16}$, and $R_{16'}$ are each hydrogen, such that the $\eta^3$-allyl ligand is unsubstituted. In other embodiments, the $\eta^3$-allyl ligand is monosubstituted with an alkyl group, such as a $C_1$-$C_4$-alkyl group (i.e., only one of $R_{14}$, $R_{14'}$, $R_{15}$, $R_{16}$, and $R_{16'}$ is an alkyl group while the remaining groups are each hydrogen). In yet other embodiments, $R_{14}$ and $R_{16}$ are independently silyl and $R_{14'}$ and $R_{16'}$ are each hydrogen.

Any of the aforementioned metal complexes disclosed herein, including the metal complexes of Formulas I, IA, IB, IC, or ID, may be provided as solvates. For example, one or more solvent molecules may be associated with the metal complex, for instance, by coordination to the metal center as an additional ligand or ligands. As will be appreciated by those of skill in the art, solvates may be formed in the process of synthesizing the metal complex, isolation of the metal complex, and/or purification of the metal complex. In some embodiments, the solvate is an ether solvate, an amine solvate or a hydrocarbon solvate.

The metal complexes of Formulas I, IA, IB, IC, and ID (and solvated forms thereof) may be prepared by any number of methods, depending on the identity of the particular metal complex of interest. In general, the metal complexes may be prepared by reaction of the ligand of Formula II or conjugate acid thereof with an appropriate metal salt (e.g., a Group 7-10 metal salt or copper salt), with optional further reaction or co-reaction with other ligands or ligand precursors. As will be appreciated by those of skill in the art, the ligand of Formula II may be prepared by the deprotonation of the corresponding conjugate acid of the ligand of Formula II with a suitable base such as, for example, n-butyllithium or sodium hydride. Suitable metal salts include, but are not limited to metal halides, metal psuedohalides, metal nitrates, metal sulfates, metal carbonates, metal acetates, metal alkane- or arenesulfonates (e.g., metal triflates, metal tosylates), metal amides, metal silylamides (e.g., bis(trialkylsilylamido)metals such as bis(trialkylsilylamido)manganese). In some embodiments, the metal salt is a Group 7-10 metal salt or copper salt. In particular embodiments, the metal salt is manganese salt, such as manganese(II) chloride, manganese(II) bromide, manganese(II) iodide, manganese(II) nitrate, manganese(II) acetate, manganese(II) sulfate, manganese(II) carbonate, manganese(II) perchlorate, manganese(II) trifluoromethanesulfonate, or bis(trimethylsilylamido)manganese.

As illustrated in Scheme 1, bis(trialkylsilylamido)metals are particularly useful in the preparation of metal complexes of Formulas I, IA, IB, IC, and ID; such metal salts are generally sufficiently basic as to allow for the direct use of the conjugate acid of the ligand of Formula II (stated differently, the need to pre-form the ligand of Formula II via deprotonation of the corresponding conjugate acid is obviated). Of course and as will be appreciated by those of skill in the art, less basic metal salts such as metal halides may be employed in conjunction with preformed ligand of Formula II (typically as a lithium or sodium salt).

Scheme 1

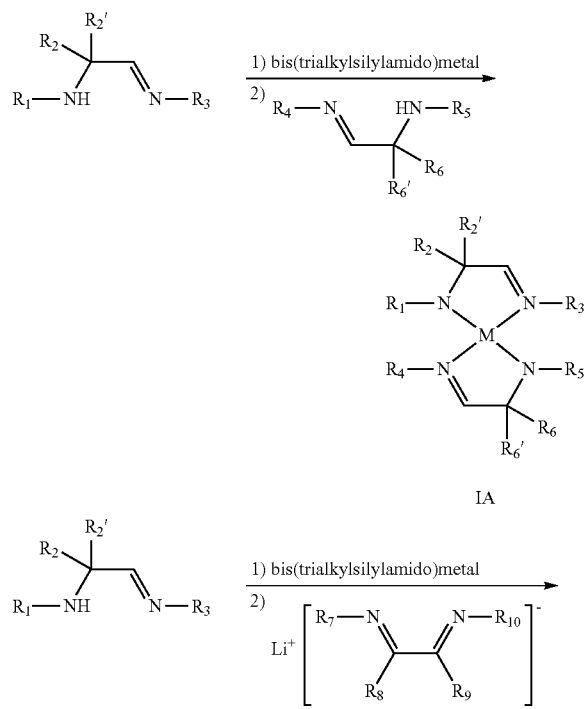

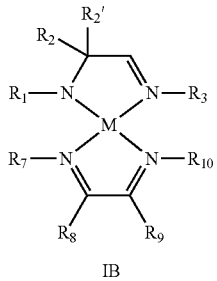

IB

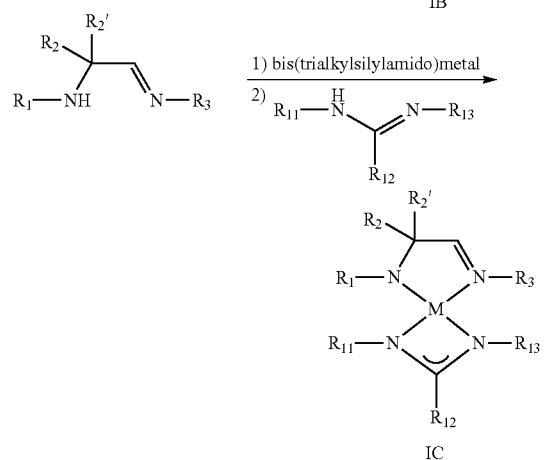

IC

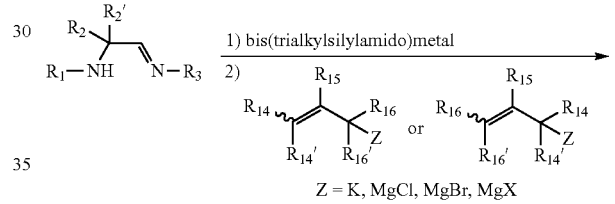

Z = K, MgCl, MgBr, MgX

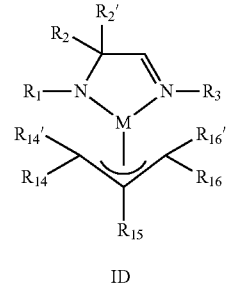

ID

The metal complexes described herein are generally synthesized in the presence of one or more solvents. Examples of suitable solvents include, but are not limited to, ethers (e.g., diethyl ether, tetrahydrofuran, 1,2-dimethoxyethane, 1,4-dioxane, and the like) and aromatic hydrocarbons (e.g., benzene, toluene, and the like).

The metal complexes described herein may be isolated from the reaction mixture from which they are formed and optionally purified using standard techniques known in the art. Such techniques include, but are not limited to, centrifugation, filtration, extraction, recrystallization, chromatography, sublimation, distillation, and the like. Depending on the manner of preparation of a particular metal complex, the identity of solvent(s) used in the complexation reaction, and the method of isolation and purification, it is possible that the metal complex may be isolated as a solvated form. For instance, the metal complexes may be isolated as solvates of any of the aforementioned solvents, or as solvates of any byproducts formed in the complexation reaction.

Ligands and ligand precursors (e.g., amidoimine, aminoimine, diazabutadiene, amidine, amidinate, and allyl ligands or related ligand precursors such as those shown in Scheme 1) are commercially available or may be synthesized according to known procedures (e.g., *Inorg. Chem.* 2009, 48, 7639-7644), or simple modifications such known procedures which are well within the grasp of the person of ordinary skill.

Figure 2:
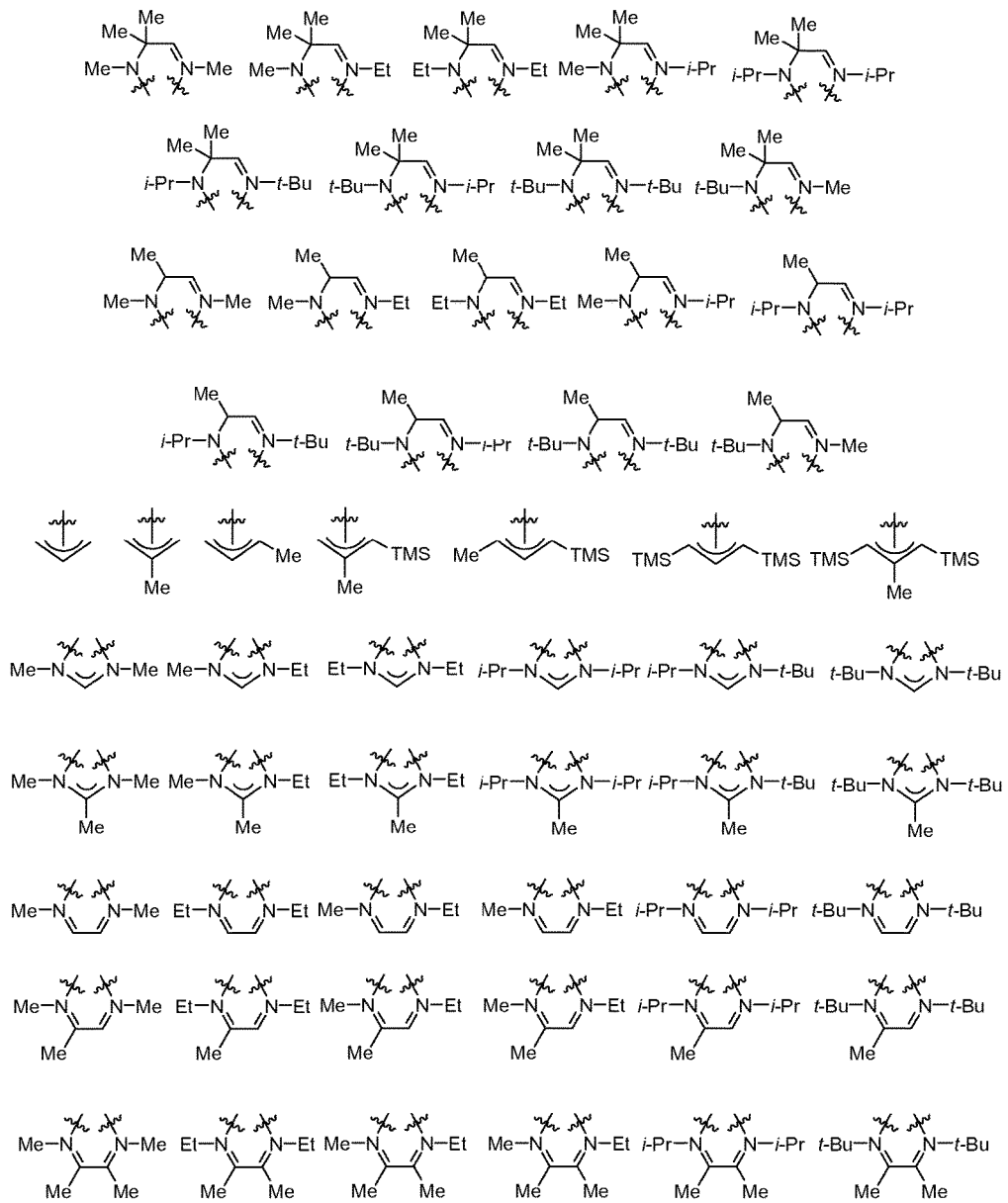
FIG. 2 illustrates various embodiments of ligands, L, which may be bonded to any one of the metal complexes of Formula I illustrated in FIG. 1, in any combination.

FIG. 1 illustrates various embodiments of metal complexes of Formula I, where M is a metal selected from Groups 7-10 of the periodic table or is copper. In some embodiments, M selected from the group consisting of manganese, cobalt, nickel, and copper. In particular embodiments, M is manganese. FIG. 2 illustrates various embodiments of ligands, L, which may be bonded to any of the metal complexes of Formula I illustrated in FIG. 1 (in any combination) such as to provide metal complexes of Formulas IA, IB, IC, and ID.

The metal complexes provided herein may be used to prepare metal-containing films such as, for example, elemental manganese and manganese nitride films, with smooth morphology. Thus, according to another aspect, a method for forming a metal-containing film by a vapor deposition process is provided, the method employing at least one of the metal complexes disclosed herein, such as those of Formulas I, IA, IB, IC, ID, or solvates thereof. The film-forming method may include, for example, (1) vaporizing the metal complex and (2) delivering and/or exposing the metal complex to a substrate surface or passing the metal complex over a substrate surface (and/or decomposing the one metal complex on the substrate surface).

A variety of substrates can be used in the deposition methods disclosed herein. For example, metal complexes as disclosed herein may be delivered to, passed over, or deposited on a variety of substrates or surfaces thereof such as, but not limited to, silicon, crystalline silicon, Si(100), Si(111), silicon oxide, glass, strained silicon, silicon on insulator (SOI), doped silicon or silicon oxide(s) (e.g., carbon doped silicon oxides), silicon nitride, germanium, gallium arsenide, tantalum, tantalum nitride, aluminum, copper, ruthenium, titanium, titanium nitride, tungsten, tungsten nitride, and any number of other substrates commonly encountered in nanoscale device fabrication processes (e.g., semiconductor fabrication processes). As will be appreciated by those of skill in the art, substrates may be exposed to a pretreatment process to polish, etch, reduce, oxidize, hydroxylate, anneal and/or bake the substrate surface. In one or more embodiments, the substrate surface contains a hydrogen-terminated surface.

In certain embodiments, the metal complex may be dissolved in a suitable solvent such as a hydrocarbon or an amine solvent to facilitate the vapor deposition process. Appropriate hydrocarbon solvents include, but are not limited to, aliphatic hydrocarbons, such as hexane, heptane and nonane; aromatic hydrocarbons, such as toluene and xylene; and aliphatic and cyclic ethers, such as diglyme, triglyme, and tetraglyme. Examples of appropriate amine solvents include, without limitation, octylamine and N,N-dimethyldodecylamine. For example, the metal complex may be dissolved in toluene to yield a solution with a concentration from about 0.05 M to about 1 M.

In another embodiment, the at least one metal complex may be delivered "neat" (undiluted by a carrier gas) to a substrate surface.

In one embodiment, the vapor deposition process is chemical vapor deposition.

In another embodiment, the vapor deposition process is atomic layer deposition.

The ALD and CVD methods encompass various types of ALD and CVD processes such as, but not limited to, continuous or pulsed injection processes, liquid injection processes, photo-assisted processes, plasma-assisted, and plasma-enhanced processes. For purposes of clarity, the methods of the present technology specifically include direct liquid injection processes. For example, in direct liquid injection CVD ("DLI-CVD"), a solid or liquid metal complex may be dissolved in a suitable solvent and the solution formed therefrom injected into a vaporization chamber as a means to vaporize the metal complex. The vaporized metal complex is then transported/delivered to the substrate surface. In general, DLI-CVD may be particularly useful in those instances where a metal complex displays relatively low volatility or is otherwise difficult to vaporize.

In one embodiment, conventional or pulsed CVD is used to form a metal-containing film vaporizing and/or passing the at least one metal complex over a substrate surface. For conventional CVD processes see, for example Smith, Donald (1995). *Thin-Film Deposition: Principles and Practice.* McGraw-Hill.

In one embodiment, CVD growth conditions for the metal complexes disclosed herein include, but are not limited to:
  a. Substrate temperature: 50-600° C.
  b. Evaporator temperature (metal precursor temperature): 0-200° C.
  c. Reactor pressure: 0-100 Torr
  d. Argon or nitrogen carrier gas flow rate: 0-500 sccm
  e. Oxygen flow rate: 0-500 sccm
  f. Hydrogen flow rate: 0-500 sccm
  g. Run time: will vary according to desired film thickness In another embodiment, photo-assisted CVD is used to form a metal-containing film by vaporizing and/or passing at least one metal complex disclosed herein over a substrate surface.

In a further embodiment, conventional (i.e., pulsed injection) ALD is used to form a metal-containing film by vaporizing and/or passing at least one metal complex disclosed herein over a substrate surface. For conventional ALD processes see, for example, George S. M., et al. *J. Phys. Chem.,* 1996, 100, 13121-13131.

In another embodiment, liquid injection ALD is used to form a metal-containing film by vaporizing and/or passing at least one metal complex disclosed herein over a substrate surface, wherein at least one metal complex is delivered to the reaction chamber by direct liquid injection as opposed to vapor draw by a bubbler. For liquid injection ALD processes see, for example, Potter R. J., et al., *Chem. Vap. Deposition,* 2005, 11(3), 159-169.

Examples of ALD growth conditions for metal complexes disclosed herein include, but are not limited to:
  a. Substrate temperature: 0-400° C.
  b. Evaporator temperature (metal precursor temperature): 0-200° C.
  c. Reactor pressure: 0-100 Torr
  d. Argon or nitrogen carrier gas flow rate: 0-500 sccm
  e. Reactive gas flow rate: 0-500 sccm
  f. Pulse sequence (metal complex/purge/reactive gas/purge): will vary according to chamber size
  g. Number of cycles: will vary according to desired film thickness In another embodiment, photo-assisted ALD is used to form a metal-containing film by vaporizing and/or passing at least one metal complex disclosed herein over a substrate surface. For photo-assisted ALD processes see, for example, U.S. Pat. No. 4,581,249.

In another embodiment, plasma-assisted ALD is used to form a metal-containing film by vaporizing and/or passing at least one metal complex disclosed herein over a substrate surface.

In another embodiment, a method of forming a metal-containing film on a substrate surface comprises: during an ALD process, exposing a substrate to a vapor phase metal complex according to one or more of the embodiments described herein, such that a layer is formed on the surface comprising the metal complex bound to the surface by the metal center (e.g., manganese); during an ALD process, exposing the substrate having bound metal complex with a co-reactant such that an exchange reaction occurs between the bound metal complex and co-reactant, thereby dissociating the bound metal complex and producing a first layer of elemental metal on the surface of the substrate; and sequentially repeating the ALD process and the treatment.

The reaction time, temperature and pressure are selected to create a metal-surface interaction and achieve a layer on the surface of the substrate. The reaction conditions for the ALD reaction will be selected based on the properties of the metal complex. The deposition can be carried out at atmospheric pressure but is more commonly carried out at a reduced pressure. The vapor pressure of the metal complex should be low enough to be practical in such applications. The substrate temperature should be high enough to keep the bonds between the metal atoms at the surface intact and to prevent thermal decomposition of gaseous reactants. However, the substrate temperature should also be high enough to keep the source materials (i.e., the reactants) in the gaseous phase and to provide sufficient activation energy for the surface reaction. The appropriate temperature depends on various parameters, including the particular metal complex used and the pressure. The properties of a specific metal complex for use in the ALD deposition methods disclosed herein can be evaluated using methods known in the art, allowing selection of appropriate temperature and pressure for the reaction. In general, lower molecular weight and the presence of functional groups that increase the rotational entropy of the ligand sphere result in a melting point that yields liquids at typical delivery temperatures and increased vapor pressure.

An optimized metal complex for use in the deposition methods will have all of the requirements for sufficient vapor pressure, sufficient thermal stability at the selected substrate temperature and sufficient reactivity to produce a reaction on the surface of the substrate without unwanted impurities in the thin film. Sufficient vapor pressure ensures that molecules of the source compound are present at the substrate surface in sufficient concentration to enable a complete self-saturating reaction. Sufficient thermal stability ensures that the source compound will not be subject to the thermal decomposition which produces impurities in the thin film.

Thus, the metal complexes disclosed herein utilized in these methods may be liquid, solid, or gaseous. Typically, the metal complexes are liquids or solids at ambient temperatures with a vapor pressure sufficient to allow for consistent transport of the vapor to the process chamber.

In one embodiment, an elemental metal, a metal nitride, a metal oxide, or a metal silicide film can be formed by delivering for deposition at least one metal complex as disclosed herein, independently or in combination with a co-reactant. In this regard, the co-reactant may be deposited or delivered to or passed over a substrate surface, independently or in combination with the at least one metal complex. As will be readily appreciated, the particular co-reactant used will determine the type of metal-containing film is obtained. Examples of such co-reactants include, but are not limited to hydrogen, hydrogen plasma, oxygen, air, water, an alcohol, $H_2O_2$, $N_2O$, ammonia, a hydrazine, a borane, a silane, ozone, or a combination of any two or more thereof. Examples of suitable alcohols include, without limitation, methanol, ethanol, propanol, isopropanol, tert-butanol, and the like. Examples of suitable boranes include, without limitation, hydridic (i.e., reducing) boranes such as borane, diborane, triborane and the like. Examples of suitable silanes include, without limitation, hydridic silanes such as silane, disilane, trisilane, and the like. Examples of suitable hydrazines include, without limitation, hydrazine ($N_2H_4$), a hydrazine optionally substituted with one or more alkyl groups (i.e., an alkyl-substituted hydrazine) such as methylhydrazine, tert-butylhydrazine, N,N- or N,N'-dimethylhydrazine, a hydrazine optionally substituted with one or more aryl groups (i.e., an aryl-substituted hydrazine) such as phenylhydrazine, and the like.

In one embodiment, the metal complexes disclosed herein are delivered to the substrate surface in pulses alternating with pulses of an oxygen-containing co-reactant as to provide metal oxide films. Examples of such oxygen-containing co-reactants include, without limitation, $H_2O$, $H_2O_2$, $O_2$, ozone, air, i-PrOH, t-BuOH, or $N_2O$.

In other embodiments, a co-reactant comprises a reducing reagent such as hydrogen. In such embodiments, an elemental metal film is obtained. In particular embodiments, the elemental metal film consists of, or consists essentially of, pure metal. Such a pure metal film may contain more than about 80, 85, 90, 95, or 98% metal. In even more particular embodiments, the elemental metal film is a manganese film.

In other embodiments, a co-reactant is used to form a metal nitride film by delivering for deposition at least one metal complex as disclosed herein, independently or in combination, with a co-reactant such as, but not limited to, ammonia, a hydrazine, and/or other nitrogen-containing compounds (e.g., an amine) to a reaction chamber. A plurality of such co-reactants may be used. In further embodiments, the metal nitride film is a manganese nitride film of the formula $MnN_x$, where the variable "x" is in the range of about 0.1, 0.2, or 0.25 to about 1, 2, 3, or 4, or in the range of about 0.2 to about 2, or in the range of about 0.25 to about 1.

In another embodiment, a mixed-metal film can be formed by a vapor deposition process which vaporizes at least one metal complex as disclosed herein in combination, but not necessarily at the same time, with a second metal complex comprising a metal other than that of the at least one metal complex disclosed herein.

In a particular embodiment, the methods of the present technology are utilized for applications such as dynamic random access memory (DRAM) and complementary metal oxide semi-conductor (CMOS) for memory and logic applications, on substrates such as silicon chips.

Any of the manganese complexes disclosed herein may be used to prepare thin films of manganese metal, manganese oxide, manganese nitride, and/or manganese silicide. Such films may find application as oxidation catalysts, anode materials (e.g., SOFC or LIB anodes), conducting layers, sensors, diffusion barriers/coatings, super- and non-super-conducting materials/coatings, tribological coatings, and/or, protective coatings. It is understood by one of ordinary skill in the art that the film properties (e.g., conductivity) will depend on a number of factors, such as the metal(s) used for deposition, the presence or absence of co-reactants and/or co-complexes, the thickness of the film created, the parameters and substrate employed during growth and subsequent processing.

In particular embodiments, deposited elemental manganese or manganese nitride films can be used as an alternative diffusion barrier in the back-end-of-line copper interconnections to replace currently used tantalum nitride. The deposition approaches described herein can be integrated with the deposition of tantalum nitride to generate manganese-doped tantanlum nitride or tantalum doped with manganese nitride. Manganese can react with dielectric underlayers to form manganese silicates as the barrier. Without being bound to any particular theory of operation, it is believed that the manganese nitride is not only the diffusion barrier but also promotes the adhesion between copper and the dielectrics. Therefore, in some embodiments, the methods further comprise depositing copper over the manganese-containing film.

Reference throughout this specification to "one embodiment," "certain embodiments," "one or more embodiments" or "an embodiment" means that a particular feature, structure, material, or characteristic described in connection with the embodiment is included in at least one embodiment of the present technology. Thus, the appearances of the phrases such as "in one or more embodiments," "in certain embodiments," "in one embodiment" or "in an embodiment" in various places throughout this specification are not necessarily referring to the same embodiment of the present technology. Furthermore, the particular features, structures, materials, or characteristics may be combined in any suitable manner in one or more embodiments.

Although the present technology herein has been described with reference to particular embodiments, it is to be understood that these embodiments are merely illustrative of the principles and applications of the present technology. It will be apparent to those skilled in the art that various modifications and variations can be made to the method and apparatus of the present technology without departing from the spirit and scope of the present technology. Thus, it is intended that the present technology include modifications and variations that are within the scope of the appended claims and their equivalents. The present technology, thus generally described, will be understood more readily by reference to the following examples, which is provided by way of illustration and is not intended to be limiting.

EXAMPLES

Unless otherwise noted, all synthetic manipulations are performed under an inert atmosphere (e.g., purified nitrogen or argon) using techniques for handling air-sensitive materials commonly known in the art (e.g., Schlenk techniques).

Example 1A: Preparation of Complex 1 (a Homoleptic Complex of Formula IA)

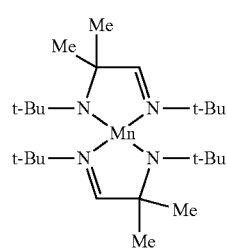

To a solution of bis(trimethylsilylamido)manganese (10 g, 0.0266 mol) in toluene (200 mL) is added (t-Bu)NHCMe$_2$CH=N(t-Bu) (10.6 g, 0.053 mol) by transfer cannula. The resulting mixture is refluxed for 24 hours. The solvent and hexamethyldisilazane by-product are then removed under reduced pressure to provide complex 1 which may be further purified by distillation or sublimation under reduced pressure.

The ligand precursor (t-Bu)NHCMe$_2$CH=N(t-Bu) can be prepared by α-bromination of isobutyraldehyde (with for example, 1,4-dioxane-bromine complex) followed by reaction with excess tert-butylamine in THF. The crude ligand precursor is isolated and purified using standard techniques.

Example 1B: Preparation of Complex 2 (a Heteroleptic Complex of Formula IA)

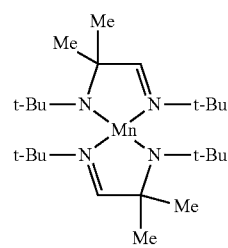

To a solution of bis(trimethylsilylamido)manganese (10 g, 0.0266 mol) in toluene (200 mL) is added (t-Bu)NHCMe$_2$CH=N(t-Bu) (5.3 g, 0.0266 mol) by transfer cannula. The resulting mixture is refluxed for 24 hours. The solvent and hexamethyldisilazane by-product are then removed under reduced pressure. The resulting intermediate is then dissolved in toluene and treated with (i-Pr)NHCMe$_2$CH=N(t-Bu) (4.9 g, 0.0266 mol)), refluxing for a further 24 hours. The solvent and hexamethyldisilazane by-product are then removed under reduced pressure to provide complex 2 which may be further purified by distillation or sublimation under reduced pressure.

The ligand precursor (i-Pr)NHCMe$_2$CH=N(t-Bu) can be prepared by α-bromination of isobutyraldehyde (with for example, 1,4-dioxane-bromine complex) followed by reaction with excess isopropylamine in THF. Subsequent treatment with excess tert-butylamine in THF provides the crude ligand precursor which is isolated and purified using standard techniques.

Example 2: Preparation of Complex 3 (a Complex of Formula IB)

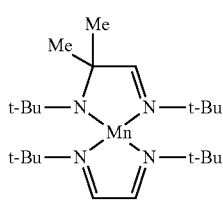

To a solution of bis(trimethylsilylamido)manganese (10 g, 0.0266 mol) in toluene is added (t-Bu)NHCMe$_2$CH=N(t-

Bu) ligand (5.3 g, 0.0266 mol) by transfer cannula. The resulting mixture is refluxed for 24 hours. The solvent and hexamethyldisilazane by-product are then removed under reduced pressure. Under argon, the intermediate is dissolved in THF (100 mL) and a solution of Li[(t-Bu)N=CHCH=N(t-Bu)] (4.7 g, 0.027 mol; prepared from (t-Bu)N=CHCH=N(t-Bu) and freshly cut Li metal in THF) in THF (100 mL) is added. The mixture is stirred at room temperature overnight. The solvent and lithium hexamethyldisilazide by-product are then removed under reduced pressure to provide complex 3 which may be further purified by distillation or sublimation under reduced pressure.

Example 3: Preparation of Complex 4 (a Complex of Formula IC)

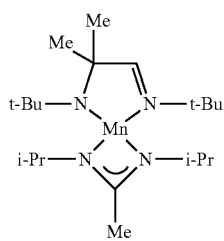

To a solution of bis(trimethylsilylamido)manganese (10 g, 0.0266 mol) in toluene (200 mL) is added (t-Bu)NHCMe$_2$CH=N(t-Bu) ligand (5.3 g, 0.0266 mol) by transfer cannula. The resulting mixture is refluxed for 24 hours. The solvent and hexamethyldisilazane by-product are then removed under reduced pressure. The resulting intermediate is then dissolved in toluene and treated with (i-Pr)N=C(Me)NH(i-Pr) (3.8 g, 0.027 mol), refluxing for a further 24 hours. The solvent and hexamethyldisilazane by-product are then removed under reduced pressure to provide complex 4 which may be further purified by distillation or sublimation under reduced pressure.

Example 4: Preparation of Complex 5 (a Complex of Formula ID)

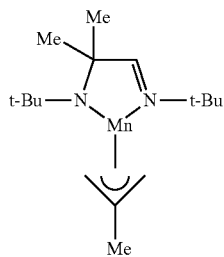

To a suspension of manganese chloride (1 equiv) in THF at −78° C. is added 2 equiv of K[CH$_2$C(CH$_3$)CH$_2$] or [CH$_2$C(CH$_3$)CH$_2$]MgBr in THF or diethyl ether. The mixture is stirred for several hours, until the solid dissolves and a color change is observed. Then, 1 equiv of (t-Bu)NHCMe$_2$CH=N(t-Bu) ligand is added by syringe and the mixture allowed to warm to room temperature slowly. The solvent is then removed under reduced pressure and the residue extracted into hexane. The mixture is then filtered by cannula and then the solvent removed under reduced pressure to provide complex 5 which may be further purified by distillation or sublimation under reduced pressure.

Example 5: Deposition of Elemental Manganese Metal Films

First, a substrate surface may be placed in an atomic layer deposition chamber. The substrate surface is then contacted with a manganese precursor, for example one of manganese complexes 1-5. Excess, unreacted manganese precursor is then purged from the reaction chamber. Then, hydrogen gas is flowed into the chamber to the substrate surface. The manganese precursor, which is bound to the substrate surface, undergoes reduction, leaving a manganese film which consists essentially of manganese metal. Excess manganese precursor is then purged from the chamber. The process can be repeated until a film of desired thickness is achieved.

Example 6: Deposition of Manganese Nitride Films

First, a substrate surface may be placed in an atomic layer deposition chamber. The substrate surface is then contacted with a manganese precursor, for example one of the manganese complexes 1-5. Excess, unreacted manganese precursor is then purged from the reaction chamber. Then, ammonia gas is flowed into the chamber to the substrate surface. The manganese precursor, which is bound to the substrate surface, reacts with the ammonia gas, leaving a film comprising manganese nitride. Excess manganese precursor is then purged from the chamber. The process can be repeated until a film of desired thickness is achieved.

All publications, patent applications, issued patents and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The words "comprise", "comprises", and "comprising" are to be interpreted inclusively rather than exclusively.

What is claimed is:
1. A metal complex of Formula I:

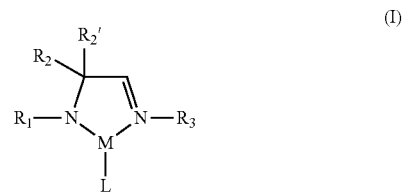

wherein
R$_1$, R$_2$, R$_{2'}$, and R$_3$ are independently selected from the group consisting of an alkyl group and an aryl group;
M is a metal selected from Groups 7-10 of the periodic table or is copper; and
L is at least one ligand selected from the group consisting of a diazabutadiene ligand, an amidinate ligand, and an allyl ligand.
2. The metal complex of claim 1, wherein M is selected from the group consisting of manganese, cobalt, nickel, and copper; and $R_1$, $R_2$, $R_{2'}$, and $R_3$ are independently selected from the group consisting of $C_1$-$C_4$-alkyl group and $C_6$-$C_{10}$-aryl group.

3. The metal complex of claim 1, wherein $R_2$ and $R_{2'}$ are each methyl.

4. The metal complex of claim 1, wherein L comprises an $\eta^3$-allyl ligand.

5. A metal complex of Formula IB:

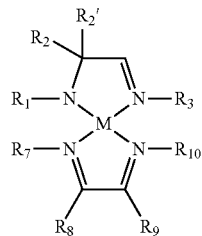

(IB)

wherein
$R_1$, $R_2$, $R_{2'}$ and $R_3$ are independently selected from the group consisting of an alkyl group and an aryl group;
$R_7$, $R_8$, $R_9$, and $R_{10}$ are independently selected from the group consisting of hydrogen, an alkyl group, and an aryl group; and
M is a metal selected from Groups 7-10 of the periodic table or is copper.

6. The metal complex of claim 5, wherein M is selected from the group consisting of manganese, cobalt, nickel, and copper; and wherein $R_1$, $R_2$, $R_{2'}$ and $R_3$ are independently selected from the group consisting of $C_1$-$C_4$-alkyl group and $C_6$-$C_{10}$-aryl group; and $R_7$, $R_8$, $R_9$, and $R_{10}$ are independently selected from the group consisting of hydrogen, $C_1$-$C_4$-alkyl group, and $C_6$-$C_{10}$-aryl group.

7. The metal complex of claim 5, wherein $R_2$ and $R_{2'}$ are each methyl and $R_8$ and $R_9$ are each hydrogen.

8. A metal complex of Formula IC:

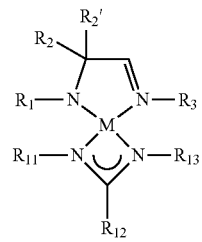

(IC)

wherein
$R_1$, $R_2$, $R_{2'}$, $R_3$, $R_{11}$, $R_{12}$, and $R_{13}$ are independently selected from the group consisting of hydrogen, an alkyl group, and an aryl group; and
M is a metal selected from Groups 7-10 of the periodic table or is copper.

9. The metal complex of claim 8, wherein M is selected from the group consisting of manganese, cobalt, nickel, and copper; and wherein $R_1$, $R_2$, $R_{2'}$, $R_3$, $R_{11}$, $R_{12}$, and $R_{13}$ are independently selected from the group consisting of hydrogen, $C_1$-$C_4$-alkyl group and $C_6$-$C_{10}$-aryl group.

10. The metal complex of claim 8, wherein $R_2$ and $R_{2'}$ are each methyl.

11. A metal complex of Formula ID:

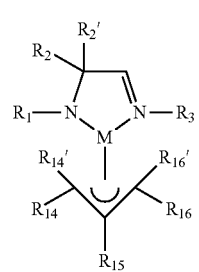

(ID)

wherein
$R_1$, $R_2$, $R_{2'}$, and $R_3$ are independently selected from the group consisting of an alkyl group and an aryl group;
$R_{14}$, $R_{14'}$, $R_{15}$, $R_{16}$, and $R_{16'}$ are independently selected from the group consisting of hydrogen, an alkyl group, an aryl group, and silyl group; and
M is a metal selected from Groups 7-10 of the periodic table or is copper.

12. The metal complex of claim 11, wherein M is selected from the group consisting of manganese, cobalt, nickel, and copper; $R_1$, $R_2$, $R_{2'}$, and $R_3$ are independently selected from the group consisting of $C_1$-$C_4$-alkyl group and $C_6$-$C_{10}$-aryl group; and
$R_{14}$, $R_{14'}$, $R_{15}$, $R_{16}$, and $R_{16'}$ are independently selected from the group consisting of hydrogen, $C_1$-$C_4$-alkyl group, $C_6$-$C_{10}$-aryl group, and tri($C_1$-$C_4$-alkyl)silyl group.

13. The metal complex of claim 11, wherein $R_2$ and $R_{2'}$ are each methyl.

14. A method for forming a metal-containing film by a vapor deposition process, the method comprising vaporizing at least one metal complex corresponding in structure to Formula I:

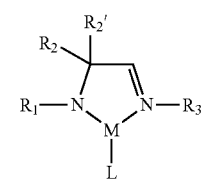

(I)

wherein
$R_1$ and $R_3$ are independently selected from the group consisting of hydrogen, an alkyl group and an aryl group;
$R_2$, and $R_{2'}$ are independently selected from the group consisting of alkyl and aryl;
M is a metal selected from Groups 7-10 of the periodic table or is copper; and
L is at least one ligand selected from the group consisting of a diazabutadiene ligand, an amidinate ligand, and an allyl ligand.

15. The method of claim 14, wherein M is selected from the group consisting of manganese, cobalt, nickel, and copper; $R_1$ and $R_3$ are independently selected from the group consisting of hydrogen, $C_1$-$C_4$-alkyl group and $C_6$-$C_{10}$-aryl group; and $R_2$ and $R_{2'}$ are independently selected from the group consisting of $C_1$-$C_4$-alkyl group and $C_6$-$C_{10}$-aryl group.

16. The method of claim 14, wherein $R_2$ and $R_{2'}$ are each methyl.

17. The method of claim 14, wherein L comprises an $\eta^3$-allyl ligand.

18. The method of claim 14, wherein the vapor deposition process is chemical vapor deposition.

19. The method of claim 18, wherein the chemical vapor deposition is pulsed chemical vapor deposition, continuous flow chemical vapor deposition, or liquid injection chemical vapor deposition.

20. The method of claim 14, wherein the vapor deposition process is atomic layer deposition.

21. The method of claim 20, wherein the atomic layer deposition is liquid injection atomic layer deposition or plasma-enhanced atomic layer deposition.

22. The method of claim 14, wherein the at least one metal complex is delivered to a substrate in pulses alternating with pulses of an oxygen source to form a metal oxide film, wherein the oxygen source is selected from the group consisting of $H_2O$, air, $O_2$ and ozone.

23. The method of claim 14, further comprising vaporizing at least one co-reactant selected from the group consisting of hydrogen, hydrogen plasma, oxygen, air, water, ammonia, a hydrazine, a borane, a silane, ozone and a combination of thereof.

24. The method of claim 14, further comprising vaporizing a hydrazine as a co-reactant, wherein the hydrazine is hydrazine ($N_2H_4$) or N,N-dimethylhydrazine.

25. The method of claim 14, wherein the method is used for a DRAM or CMOS application.

\* \* \* \* \*